United States Patent
Hollett et al.

(10) Patent No.: US 8,961,581 B2
(45) Date of Patent: Feb. 24, 2015

(54) DELIVERY SYSTEM HAVING STENT RETENTION STRUCTURE

(75) Inventors: Andrew K. Hollett, Waltham, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 499 days.

(21) Appl. No.: 13/113,265

(22) Filed: May 23, 2011

(65) Prior Publication Data

US 2011/0295265 A1 Dec. 1, 2011

Related U.S. Application Data

(60) Provisional application No. 61/348,162, filed on May 25, 2010.

(51) Int. Cl.
| | | |
|---|---|---|
| *A61F 2/07* | (2013.01) | |
| *A61M 25/01* | (2006.01) | |
| *A61F 2/95* | (2013.01) | |
| *A61F 2/94* | (2013.01) | |
| *A61M 25/00* | (2006.01) | |

(52) U.S. Cl.
CPC ............... *A61M 25/01* (2013.01); *A61F 2/95* (2013.01); *A61F 2/94* (2013.01); *A61F 2002/9505* (2013.01); *A61F 2002/9517* (2013.01); *A61M 2025/0006* (2013.01); *A61M 2025/0175* (2013.01)
USPC ............................................................ 623/1.11

(58) Field of Classification Search
CPC ............................................. A61F 2002/9586
USPC .............................. 623/1.11–1.12, 1.23
See application file for complete search history.

(56) References Cited

U.S. PATENT DOCUMENTS

| | | |
|---|---|---|
| 4,382,445 A | 5/1983 | Sommers |
| 4,592,341 A | 6/1986 | Omagari et al. |
| 4,699,611 A | 10/1987 | Bowden |
| 4,931,037 A | 6/1990 | Wetterman |
| 4,950,228 A | 8/1990 | Knapp, Jr. et al. |
| 4,955,858 A | 9/1990 | Drews |
| 4,957,479 A | 9/1990 | Roemer |
| 4,973,301 A | 11/1990 | Nissenkorn |
| 4,990,133 A | 2/1991 | Solazzo |
| 5,052,998 A | 10/1991 | Zimmon |

(Continued)

FOREIGN PATENT DOCUMENTS

EP    1 872 749    1/2008

*Primary Examiner* — Katherine Dowe
*Assistant Examiner* — Amy Shipley
(74) *Attorney, Agent, or Firm* — Seager, Tufte & Wickhem, LLC

(57) ABSTRACT

A drainage stent delivery system including an elongate shaft of a medical device, a drainage catheter or stent, and an engagement member, such as a distensible member or a compressible member, for selectively coupling the stent to the elongate shaft. The engagement member is positioned between the inner surface of the stent and the outer surface of the elongate shaft and is elongatable from a first length to a second length by longitudinal movement generally parallel to the central longitudinal axis of the stent to release the stent. At the first length, the engagement member is engaged with the inner surface of the stent to secure the stent on the elongate shaft, and at the second length the engagement member is sufficiently disengaged from the inner surface of the stent to release the stent from the elongate shaft such that the elongate shaft may be withdrawn from the stent.

21 Claims, 9 Drawing Sheets

(56) References Cited

U.S. PATENT DOCUMENTS

| | | |
|---|---|---|
| 5,152,749 A | 10/1992 | Giesy et al. |
| 5,160,341 A | 11/1992 | Brenneman et al. |
| 5,334,185 A | 8/1994 | Giesy et al. |
| 5,372,600 A | 12/1994 | Beyar et al. |
| 5,401,257 A | 3/1995 | Chevalier, Jr. et al. |
| 5,507,464 A | 4/1996 | Hamerski et al. |
| 5,599,291 A | 2/1997 | Balbierz et al. |
| 5,681,274 A | 10/1997 | Perkins et al. |
| 5,690,643 A | 11/1997 | Wijay |
| 5,921,952 A | 7/1999 | Desmond, III et al. |
| 5,921,971 A | 7/1999 | Agro et al. |
| 6,245,076 B1 * | 6/2001 | Yan ................................ 606/108 |
| 6,248,100 B1 | 6/2001 | de Toledo et al. |
| 6,264,624 B1 | 7/2001 | Desmond, III et al. |
| 6,562,024 B2 | 5/2003 | Alvarez de Toledo et al. |
| 6,620,191 B1 * | 9/2003 | Svensson ...................... 623/1.11 |
| 7,198,637 B2 | 4/2007 | Deshmukh et al. |
| 7,763,008 B2 | 7/2010 | Yu |
| 7,879,080 B2 * | 2/2011 | Sato ............................. 623/1.11 |
| 2003/0047654 A1 | 3/2003 | Johansson et al. |
| 2005/0085891 A1 | 4/2005 | Goto et al. |
| 2005/0085892 A1 | 4/2005 | Goto et al. |
| 2006/0068144 A1 | 3/2006 | Mizuno et al. |
| 2006/0276873 A1 | 12/2006 | Sato |
| 2008/0004685 A1 | 1/2008 | Seemann et al. |

\* cited by examiner

DELIVERY SYSTEM HAVING STENT RETENTION STRUCTURE

RELATED APPLICATIONS

This application claims the benefit of U.S. Provisional Application Ser. No. 61/348,162, filed May 25, 2010, the entire disclosure of which is incorporated herein by reference.

TECHNICAL FIELD

The disclosure is directed to a retention structure of a medical device. More particularly, the disclosure is directed to a stent retention structure for selectively securing a stent to a shaft of a stent delivery system. Specifically, the disclosure is directed to a retention structure for selectively securing a drainage stent to a catheter shaft of a drainage stent delivery system.

BACKGROUND

Medical devices, such as catheters, are widely used in various medical procedures to access remote anatomical locations and/or deploy therapeutic devices. One exemplary catheter system is a drainage stent delivery system configured to deliver a drainage stent (e.g., a drainage catheter) to a body lumen, such as a lumen of the biliary tree or a ureter. It may be desirable to releasably connect the drainage stent to the delivery system in order to provide the medical personnel with control over positioning and deployment of the drainage catheter in a body lumen without premature deployment of the drainage stent from the delivery system. Some exemplary drainage stent delivery systems including features for releasably connecting a drainage stent to a delivery system are disclosed in U.S. Pat. Nos. 5,921,952 and 6,562,024, the disclosures of which are incorporated herein by reference. For instance, a releasable connecting feature in the form of a flexible thread or suture may be used for releasably connecting the drainage stent to a shaft of the drainage stent delivery system.

However, a need remains to provide alternative embodiments of a retention system to releasably secure a stent, such as a vascular stent or a drainage stent, or other endoprosthesis to a stent delivery system, such as a vascular stent or drainage stent delivery system, which allows controlled positioning and deployment of the stent in a body lumen.

SUMMARY

The disclosure is directed to several alternative designs and configurations of medical device structures and assemblies including a retention structure for selectively securing a stent to a delivery system.

Accordingly, one illustrative embodiment is a stent delivery system including an elongate shaft of a medical device, a tubular stent positioned on and surrounding a distal portion of the elongate shaft, and an engagement member positioned between an inner surface of the tubular stent and an outer surface of the elongate shaft. The engagement member is configured to be elongated from a first length to a second length greater than the first length by longitudinal movement parallel to the central longitudinal axis of the tubular stent to release the tubular stent. At the first length the engagement member is engaged with the inner surface of the tubular stent to secure the tubular stent on the distal portion of the elongate shaft, and at the second length the engagement member is sufficiently disengaged from the inner surface of the tubular stent to release the tubular stent from the distal portion of the elongate shaft such that the elongate shaft may be withdrawn from the tubular stent.

Another illustrative embodiment is a stent delivery system including a stent, an elongate shaft extending distally from a handle assembly into the lumen of the stent, and an engagement member positioned between an outer surface of the elongate shaft and an inner surface of the stent. The engagement member has a first end fixedly attached to the elongate shaft and a second end opposite the first end which is translatable relative to the elongate shaft. The engagement member is configured to be elongated from a first length to a second length greater than the first length to release the stent from the elongate shaft. When at the first length a surface of the engagement member facing the inner surface of the stent is a first radial distance from a central longitudinal axis of the stent and when at the second length the surface of the engagement member facing the inner surface of the stent is a second radial distance from the central longitudinal axis of the stent. The second radial distance is less than the first radial distance.

Yet another illustrative embodiment is a method of selectively releasing a stent from an elongate shaft of a medical device. The method includes positioning a stent disposed on a distal portion of an elongate shaft of a medical device at a target location of an anatomy. An engagement member positioned between an inner surface of the stent and an outer surface of the elongate shaft is then elongated in a direction generally parallel with the central longitudinal axis such that the engagement member is elongated from a first length to a second length greater than the first length. The elongate shaft is then withdrawn from the lumen of the stent while the engagement member is elongated to the second length, thereby releasing the stent from the elongate shaft.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
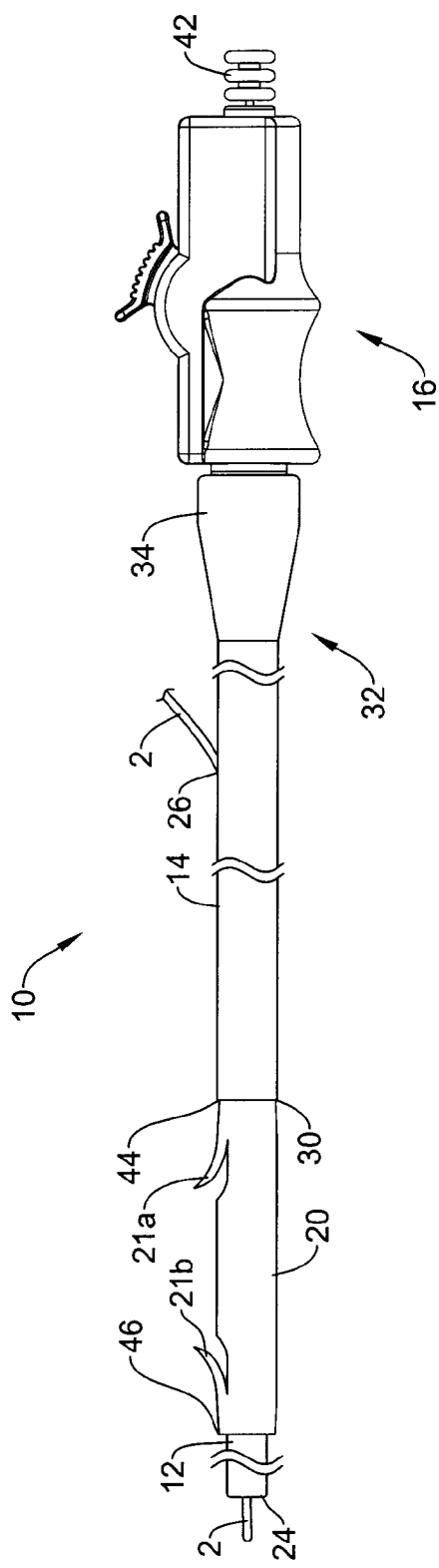
FIG. 1 is a plan view of an exemplary drainage stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "proximal" refers to a direction that is generally toward a physician during a medical procedure, while the term "distal" refers to a direction that is generally toward a target site within a patient's anatomy during a medical procedure.

As used in this specification and the appended claims, the term "body lumen" means any body passage cavity that conducts fluid, including but not limited to biliary ducts, pancreatic ducts, ureteral passages, esophagus, and blood vessels such as those of the human vasculature system.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
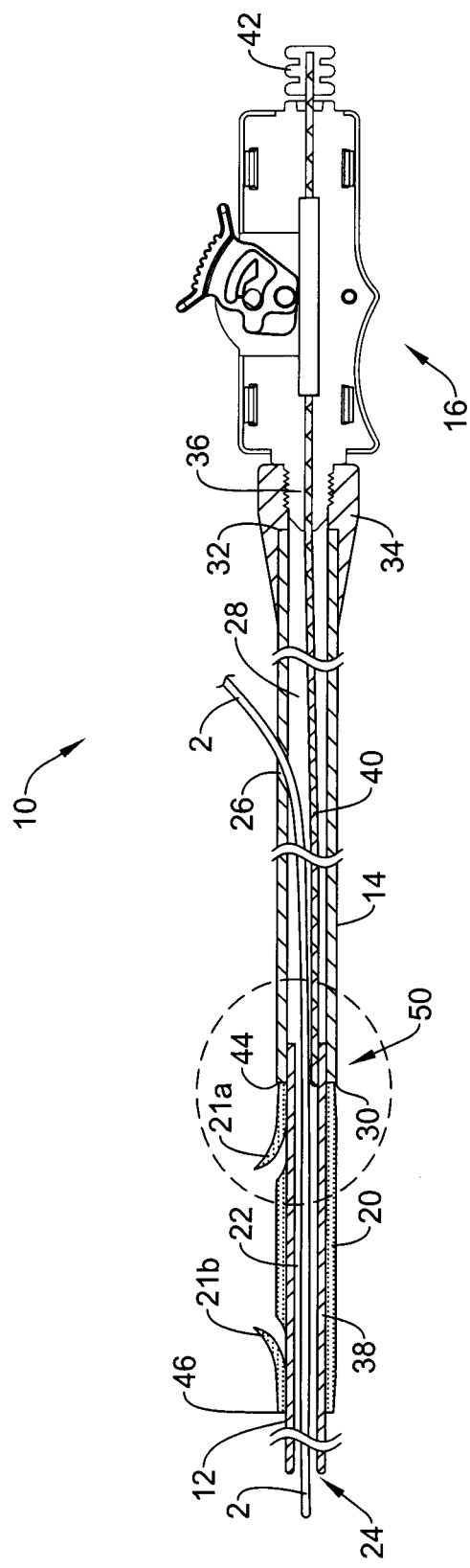
FIG. 2 is a longitudinal cross-sectional view of the drainage stent delivery system of FIG. 1.

Referring now to FIGS. 1 and 2, there is shown an exemplary medical device, illustrated as a drainage stent delivery system 10 for delivering a drainage catheter or stent 20 to an anatomical location, such as in a lumen of the biliary tree or a ureter. The drainage stent 20 may be used to bypass or drain an obstructed lumen and can be configured for long-term positioning within the lumen. The drainage stent 20 may be an elongate tubular member which is generally not expandable. The drainage stent 20 may have a proximal end 44, a distal end 46 and a lumen 48 extending through the drainage stent 20 from the proximal end 44 to the distal end 46. In some embodiments, the drainage stent 20 may include one or more, or a plurality of barbs 21, or other retention features that may help prevent migration of the drainage stent 20 when positioned in a body lumen. The illustrated drainage stent 20 includes a proximal barb 21a and a distal barb 21b. It should be understood that the terms "drainage catheter" and "drainage stent" can be used interchangeably with reference to these applications.

The drainage stent delivery system 10 is designed for use with a conventional guidewire 2 and may include a drainage stent 20, a guide catheter 12, a push catheter 14, and a handle assembly 16. The guidewire 2 may extend into a lumen 22 of the guide catheter 12 through a distal guidewire port 24 and out a proximal guidewire port 26 in a sidewall of the push catheter 14, providing the drainage stent delivery system 10 with single-operator-exchange (SOE) capabilities.

The guide catheter 12 may be slidably disposed in the lumen 28 of the push catheter 14 and extend distally from the distal end 30 of the push catheter 14. The guide catheter 12 may extend through the drainage stent 20 to a location distal of the drainage stent 20. In some embodiments, a distal portion of the push catheter 14, or a component thereof, may extend into the lumen of the drainage stent 20. In some instances, the proximal end 44 of the drainage stent 20 may abut and/or face a distal end or rim 30 of the push catheter 14, or a component thereof, while a distal portion or component of the push catheter 14 extends into the lumen of the drainage stent 20. In other embodiments, the push catheter 14, or a component thereof, may extend over the drainage stent 20, surrounding a portion of the drainage stent 20.

The drainage stent delivery system 10 may include a means for releasably connecting the drainage stent 20 to an elongate shaft of the drainage stent delivery system 10, such as the guide catheter 12 or the push catheter 14 of the drainage stent delivery system 10. When the drainage stent 20 has been properly placed, the drainage stent 20 may be disconnected from the drainage stent delivery system 10 such that the drainage stent 20 remains in the lumen when the guide catheter 12 and/or the push catheter 14 are withdrawn. Some exemplary retention mechanisms for selectively coupling the drainage stent 20 to an elongate shaft of the drainage stent delivery system 10 are further described herein. The retention mechanisms may be used to selectively deploy, reposition and/or retrieve the drainage stent 20 during a medical procedure.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means. In some instances, a component of the push catheter 14 may be longitudinally (e.g., slidably and/or rotatably) actuatable relative to another component of the push catheter 14. In such embodiments, the handle assembly 16 may be configured such that the actuatable component of the push catheter 14 may be actuated by medical personnel while the stationary component of the push catheter 14 remains stationary relative to the handle assembly 16.

The guide catheter 12 may include a distal tubular portion 38 and a proximal elongate wire 40, such as a pull wire, coupled to the distal tubular portion 38. The elongate wire 40 may be coupled to the distal tubular portion 38 at a coupling location. The elongate wire 40 may extend through the lumen 28 of the push catheter 14 to the handle assembly 16 while the distal tubular portion 38 extends through the drainage stent 20 to a location distal of the drainage stent 20. In some embodiments, the elongate wire 40 may extend through the handle assembly 16 to a location proximal of the handle assembly 16. The proximal end of the elongate wire 40 may terminate at a knob 42 which may be grasped by an operator to manipulate the guide catheter 12. An operator may selectively actuate the elongate wire 40 to effect longitudinal movement of the guide catheter 12 relative to the push catheter 14. The handle assembly 16 may also include a locking mechanism to lock the elongate wire 40 in a desired position to prevent relative movement between the guide catheter 12 and the push catheter 14. The proximal end 44 of the drainage stent 20 may abut or otherwise engage the distal end 30 of the push catheter 14 as the guide catheter 12 is actuated proximally, to inhibit movement of the drainage stent 20.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

During a medical procedure, the drainage stent delivery system 10 may be advanced to a target location in the anatomy of a patient. For instance, the drainage stent delivery system 10 may be advanced over the guidewire 2 to a target location. In some instances, the drainage stent delivery system 10 may be tracked over the guidewire 2 as the drainage stent delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

When the drainage stent 20 has been positioned at the target location in a lumen, the operator may then selectively disengage the drainage stent 20 from the drainage stent delivery system 10 and withdraw the drainage stent delivery system 10, or components thereof, proximally relative to the drainage stent 20 to deploy the drainage stent 20 at the target location. For instance, in some embodiments, elongation of an engagement member 50, 150, 250 of the drainage stent delivery system 10 relative to the drainage stent 20 may disengage or uncouple the drainage stent 20 from the drainage stent delivery system 10.

Exemplary configurations of elongating or stretching an engagement member 50, 150 to effect decoupling of the drainage stent 20 from the drainage stent delivery system 10 are further described herein, referring to the embodiments illustrated in FIGS. 3A-3C and 4A-4B. An exemplary configuration of elongating a contracted and/or compressed member 250 to effect decoupling of the drainage stent 20 from the drainage stent delivery system 10 is further described herein, referring to the embodiment illustrated in FIGS. 5A-5B.

Once the drainage stent 20 is disengaged from the guide catheter 12 and/or the push catheter 14, withdrawing the guide catheter 12 and/or the push catheter 14 proximally may release the drainage stent 20 from the drainage stent delivery system 10 in order to deploy the drainage stent 20 at the target location. Once the drainage stent 20 has been properly deployed at the target location, the drainage stent delivery system 10 may then be withdrawn. In some instances, the drainage stent delivery system 10 may also be used to reposition and/or retrieve the drainage stent 20 during a medical procedure.

Some exemplary retention structures for selectively coupling the drainage stent 20 to a component, such as an elongate shaft, of the drainage stent delivery system 10 will now be further described.

Figure 3A:
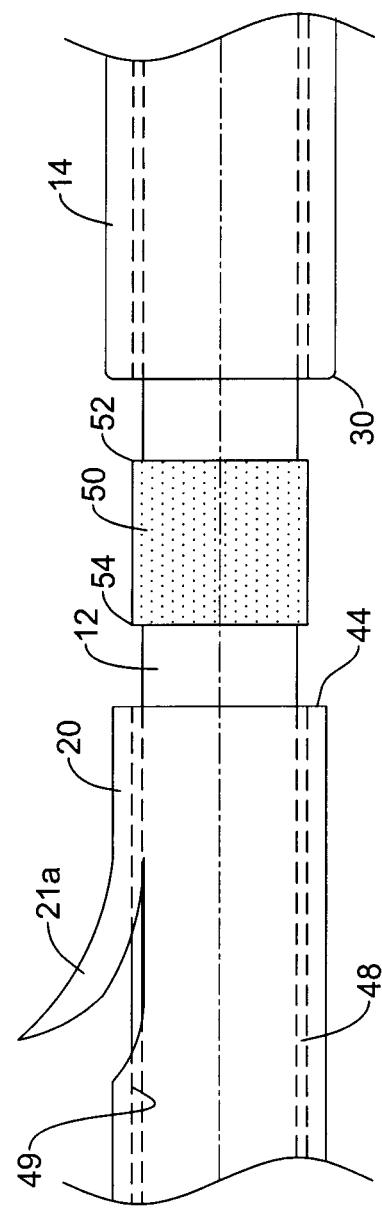
FIG. 3A is a side view of the drainage stent delivery system of FIGS. 1 and 2 illustrating an exemplary retention structure for selectively retaining the drainage stent.

FIG. 3A illustrates components of a first exemplary retention structure for selectively coupling the drainage stent 20 to an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to the push catheter 14, or another elongate shaft, in the manner described with regard to FIGS. 3A-3C.

As shown in FIG. 3A, a distal portion of the guide catheter 12 may extend distally from the distal end 30 of the push catheter 14 into and/or through the lumen 48 of the drainage stent 20. The drainage stent delivery system 10 may include an engagement member 50 positioned on the guide catheter 12 for selectively securing the drainage stent 20 to the guide catheter 12. In some instances, the engagement member 50 may be an annular sleeve circumferentially surrounding the elongate shaft of the guide catheter 12. In other embodiments, the engagement member 50 may be one or more, or a plurality of, interconnected or disconnected elongate members, such as elongated longitudinal strips, positioned on a portion of the guide catheter 12. The engagement member 50 may have a first end 52 and a second end 54 opposite the first end 52 and defining a length therebetween. The engagement member 50 may be positioned on the guide catheter 12 such that one of the first end 52 and the second end 54 is fixedly secured to the guide catheter 12 and the other of the first end 52 and the second end 54 is movable relative to the guide catheter 12. For instance, in some instances, the first end 52 (i.e., the proximal end) of the engagement member 50 may be affixed to the guide catheter 12, preventing relative movement therebetween, while the second end 54 (i.e., the distal end) of the engagement member 50 remains moveable in an axial direction (i.e., proximally or distally) relative to the guide catheter 12. In other embodiments, the second end 54 of the engagement member 50 may be affixed to the guide catheter 12, preventing relative movement therebetween, while the first end 52 of the engagement member 50 remains moveable in an axial direction (i.e., proximally or distally) relative to the guide catheter 12.

Figure 3B:
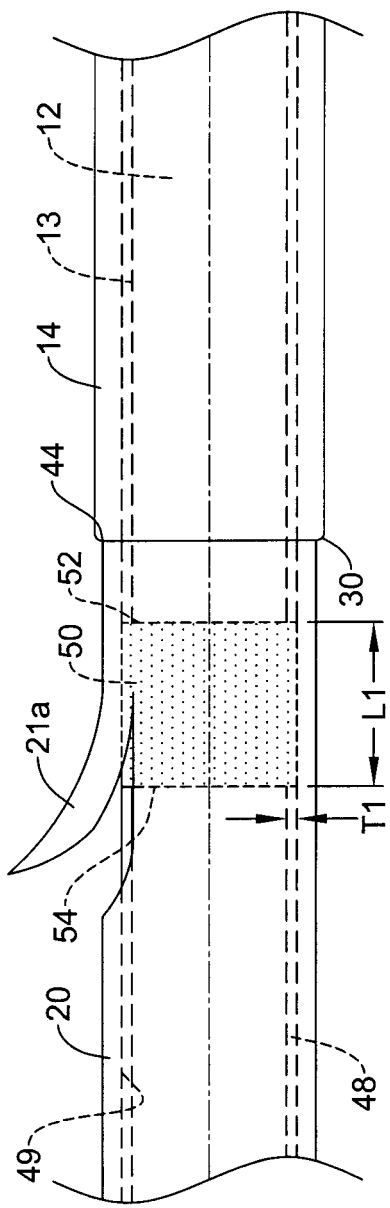
FIGS. 3B and 3C are side views illustrating the functionality of the exemplary retention structure for selectively coupling the stent to an elongate shaft of the delivery system.
Figure 3C:
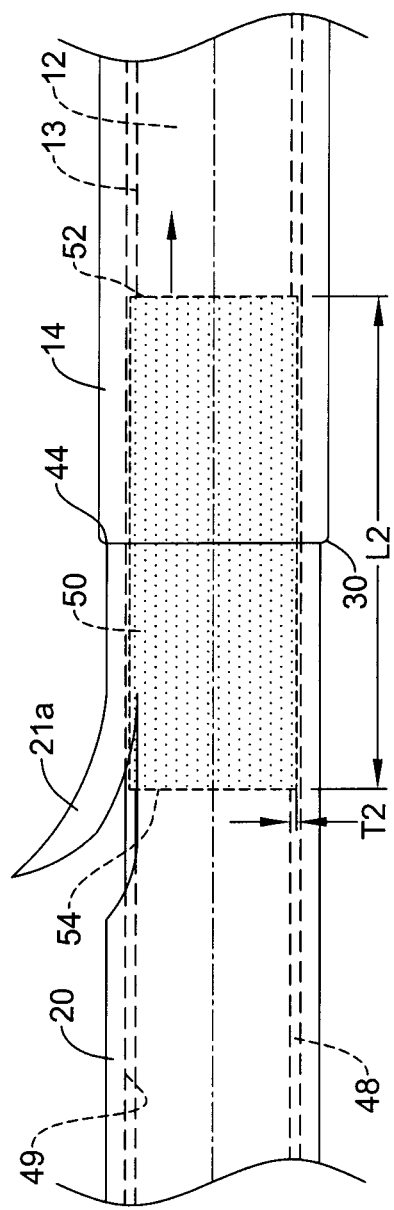

The engagement member 50 may be distensible (e.g., stretchable or elongatable) from a first length to a second length, which will be further described herein. The engagement member 50 may be formed of various stretchable materials. In some instances, as shown in FIGS. 3A-3C, the engagement member 50 may comprise a sleeve having an adhesive coating or layer on a radially outward surface of the engagement member 50. In some embodiments the sleeve may be an adhesively coated polymeric foam sleeve. Adhesion of the adhesive coating may be enhanced with surface roughening, plasma treatment, electrostatic charge, etc. It is noted that in other embodiments, such as discussed with the embodiment illustrated at FIGS. 4A and 4B, the engagement member 50 may be formed of various other materials, such as polymeric materials, silicone, rubber, or other stretchable materials, which may include an adhesive outer surface. In some embodiments, the engagement member 50 may include surface effects including, but not limited to, grooves, bumps, ridges, holes, dents, ribs, patterns, and the like.

FIGS. 3B and 3C illustrate the functionality of the engagement member 50 for selectively coupling the drainage stent 20 to an elongate shaft of the drainage stent delivery system 10.

FIG. 3B shows the drainage stent 20 selectively coupled to the guide catheter 12 with the engagement member 50 in a first position. In the first position shown in FIG. 3B, the engagement member 50 is positioned between the inner surface 49 of the drainage stent 20 and the outer surface 13 of the elongate shaft of the guide catheter 12. The surface of the engagement member 50 facing the inner surface 49 of the drainage stent 20 may be an adhesive outer surface adhered to the inner surface 49 of the drainage stent 20 to prevent disengagement of the drainage stent 20 from the guide catheter 12.

In the first position, the engagement member 50 may have a first length L1 and a first thickness T1. Length, as used herein is a dimension of the engagement member 50 measured in a direction parallel to the central longitudinal axis of the guide catheter 12 and drainage stent 20, and refers to the distance between the first end 52 and the second end 54 of the engagement member 50. Thickness, as used herein is a dimension of the engagement member 50 measured in a radial direction perpendicular to the central longitudinal axis of the guide catheter 12 and the drainage stent 20, and refers to the distance between the surface of the engagement member 50 facing the guide catheter 12 and the surface of the engagement member 50 facing the drainage stent 20.

As shown in FIG. 3B, in the first position, the first thickness T1 of the engagement member 50 may be equal to or greater than the distance between the outer surface 13 of the guide catheter 12 and the inner surface 49 of the drainage stent 20. In embodiments in which the engagement member 50 is an annular sleeve, the sleeve of the engagement member 50 has a first outer diameter at the first length L1 which is greater than or equal to the inner diameter of the drainage stent 20. So configured, the surface of the engagement member 50 facing the inner surface 49 of the drainage stent 20 is a first radial distance from the central longitudinal axis of the drainage stent 20 when at the first length L1. Thus, the surface of the engagement member 50 facing the inner surface 49 of the drainage stent 20 is engaged with the inner surface 49 of the drainage stent 20 to secure the drainage stent 20 on the distal portion of the elongate shaft of the guide catheter 12. The engagement member 50 may be adhesively bonded to the inner surface 49 of the drainage stent 20 in the first position in which the engagement member 50 is at the first length L1.

The engagement member 50 may be stretched from the first length L1 to a second length L2 by longitudinal movement generally parallel to the central longitudinal axis of the drainage stent 20 and the guide catheter 12. For instance, the engagement member 50 may be stretched from the first length L1 shown in FIG. 3B to a second length L2 shown in FIG. 3C to release the drainage stent 20 from the engagement member 50 and deploy the drainage stent 20. The second length L2 is greater than the first length L1. The Poisson's ratio of the material of the engagement member 50 may be such that as the engagement member 50 is stretched to the second length L2, the thickness of the engagement member 50 is reduced from the first thickness T1 to the second thickness T2, accordingly. For example, the Poisson's ratio of the material of the engagement member 50 may be about 0.1 to about 0.5, about 0.2 to about 0.5, about 0.25 to about 0.45, about 0.3 to about 0.45, or about 0.3 to about 0.5 in some instances.

When the engagement member 50 is stretched to the second length L2, the engagement member 50 may be sufficiently disengaged from the inner surface 49 of the drainage stent 20 to release the drainage stent 20 from the distal portion of the elongate shaft of the guide catheter 12 such that the guide catheter 12 may be withdrawn from the drainage stent 20.

As shown in FIG. 3C, the second thickness T2 of the engagement member 50 may be less than the first thickness T1 of the engagement member 50. The second thickness T2 may be less than the distance between the outer surface 13 of the guide catheter 12 and the inner surface 49 of the drainage stent 20. Thus, when the engagement member 50 is stretched to the second length L2, the surface of the engagement member 50 facing the inner surface 49 of the drainage stent 20 is a radial distance from the central longitudinal axis of the guide catheter 12 and drainage stent 20 less than the radial distance of the surface when the engagement member 50 is at the first length L1. Thus, the radial distance of the surface of the engagement member 50 when at the second length L2 may be less than the radial distance to the inner surface 49 of the drainage stent 20. In instances in which the engagement member 50 is an annular sleeve, the outer diameter of the engagement member 50 at the second length L2 may be less than the inner diameter of the drainage stent 20. Thus, the surface of the engagement member 50 facing the inner surface 49 of the drainage stent 20 is sufficiently disengaged from the inner surface 49 of the drainage stent 20 to release the drainage stent 20 from the distal portion of the elongate shaft of the guide catheter 12.

In embodiments in which the engagement member 50 includes an adhesive outer surface facing the inner surface 49 of the drainage stent 20, adhesion between the inner surface 49 of the drainage stent 20 and the engagement member 50 may be reduced as the engagement member 50 is stretched to the second length L2 from the first length L1. When the engagement member 50 is stretched to the second length L2, the engagement member 50 may be debonded from the inner surface 49 of the drainage stent 20 such that the drainage stent 20 may be released from the guide catheter 12.

The adhesive may be a stretch release adhesive, similar to a stretch release adhesive manufactured by 3M of St. Paul, Minn. and sold under the Command® brand name. The adhesive may sufficiently adhere to the inner surface 49 of the drainage stent 20 when the engagement member 50 is at the first length L1, but once the engagement member 50 is stretched to increase the surface area of the adhesive surface of the engagement member 50 sufficiently, the adhesive bonds between the engagement member 50 and the drainage stent 20 may be broken to release the drainage stent 20 from the engagement member 50.

In order to allow elongation of the engagement member 50 it may be necessary to allow at least a portion of the engagement member 50 to move longitudinally relative to the guide catheter 12. For instance, as shown in FIG. 3C, to stretch the engagement member 50 the guide catheter 12 may be actuated proximally relative to the drainage stent 20. As the guide catheter 12 is actuated proximally, the proximal end 44 of the drainage stent 20 abuts the distal end 30 of the push catheter 14, holding the drainage stent 20 from further proximal movement. As the guide catheter 12 is actuated proximally, the engagement member 50 is stretched from the first length L1 to the second length L2. To effectuate elongation of the engagement member 50, the first end 52 (proximal end) may be fixedly attached to the guide catheter 12 while the second end 54 (distal end) remains unsecured to the guide catheter 12. Thus, the first end 52 may move proximally with the guide catheter 12 (i.e., no relative movement between the first end 52 and the guide catheter 12) while the second end 54 may remain stationary with the drainage stent 20 due to adhesion to the drainage stent 20 as the guide catheter 12 is translated proximally. As the engagement member 50 is stretched, the adhesion between the adhesive surface of the engagement member 50 and the inner surface 49 of the drainage stent 20 is reduced until the adhesive surface of the engagement member 50 is ultimately released from the drainage stent 20.

It is noted that although the above discussion contemplates the guide catheter 12 being actuated in a proximal direction relative to the drainage stent 20 to effect release of the engagement member 50 from the drainage stent 20, in some instances the guide catheter 12 may be actuated distally relative to the drainage stent 20 to effect release of the engagement member 50. In such instances, the second end 54 (distal end) of the engagement member 50 may be fixedly attached to the guide catheter 12 while the first end 52 (proximal end) remains unattached and moveable relative to the guide catheter 12. Furthermore, it is contemplated that the engagement member 50 may alternatively be stretched by actuating another elongate member attached to either the first end 52 or the second end 54 of the engagement member 50. For instance, a discrete pull wire may be attached to the first end 52 of the engagement member 50 which may be pulled proximally to stretch the engagement member 50 from the first length L1 to the second length L2 while the guide catheter 12 and/or the push catheter 14 remain stationary.

Figure 4A:
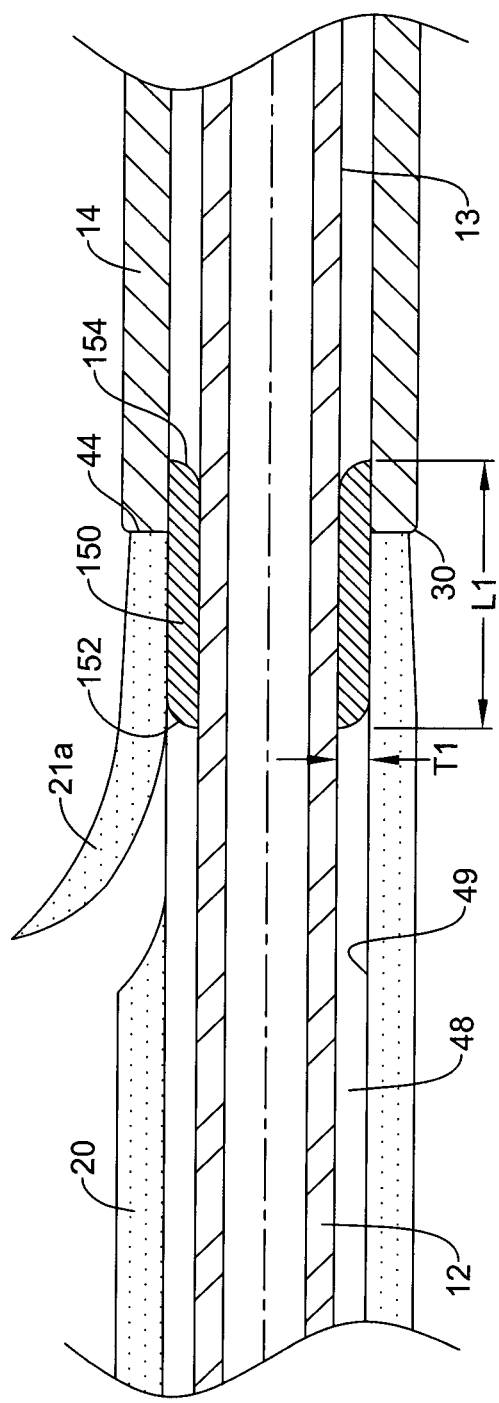
FIGS. 4A and 4B are longitudinal cross-sectional views illustrating the configuration and functionality of another retention structure for selectively coupling a stent to an elongate shaft of a delivery system.
Figure 4B:
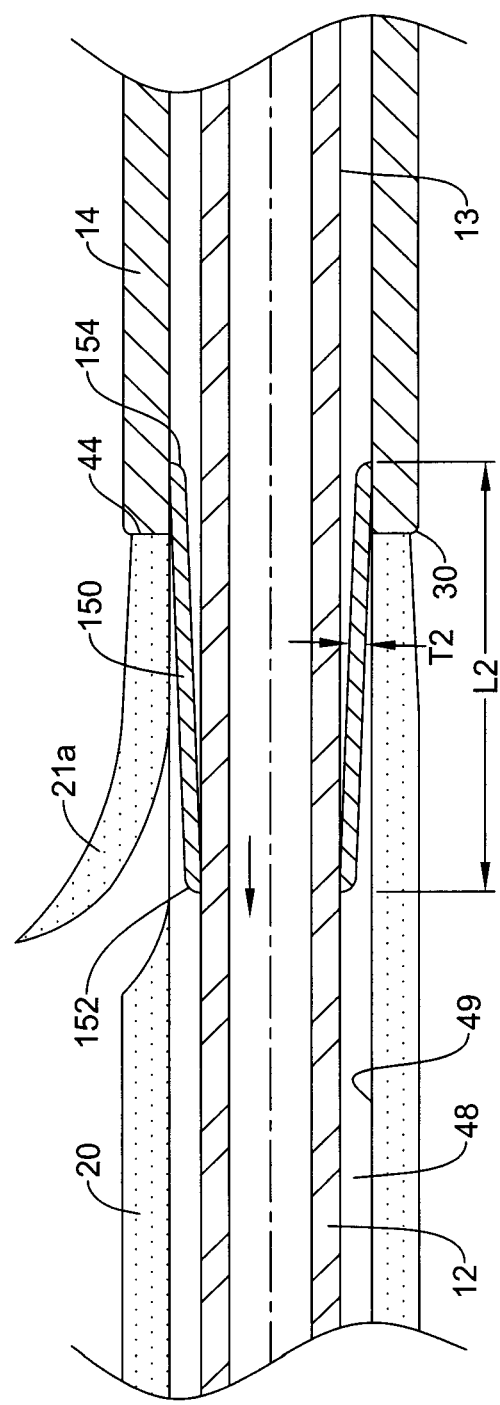

FIGS. 4A and 4B illustrate the components and functionality of a second exemplary retention structure for selectively coupling the drainage stent 20 to an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to the push catheter 14, or another elongate shaft, in the manner described with regard to FIGS. 4A and 4B.

As shown in FIG. 4A, a distal portion of the guide catheter 12 extends distally from the distal end 30 of the push catheter 14 into and/or through the lumen 48 of the drainage stent 20. The drainage stent delivery system 10 may include an engagement member 150 positioned on the guide catheter 12 for selectively securing the drainage stent 20 to the guide catheter 12. In some instances, the engagement member 150 may be an annular sleeve circumferentially surrounding the elongate shaft of the guide catheter 12. In other embodiments, the engagement member 150 may be one or more, or a plurality of, interconnected or disconnected elongate members, such as elongated longitudinal strips, positioned on a portion of the guide catheter 12. The engagement member 150 may have a first end 152 and a second end 154 opposite the first end 152 and defining a length therebetween. The engagement member 150 may be positioned on the guide catheter 12 such that one of the first end 152 and the second end 154 is fixedly secured to the guide catheter 12 and the other of the first end 152 and the second end 154 is fixedly secured to the push catheter 14. For instance, in some instances, the second end 154 (i.e., the proximal end) of the engagement member 150 may be affixed to the push catheter 14, while the first end 152 (i.e., the distal end) of the engagement member 150 may be affixed to the guide catheter 12. Thus, the first end 152 may be movable relative to the push catheter 14 by actuating the guide catheter 12 and/or the second end 154 may be movable relative to the guide catheter 12 by actuating the push catheter 14. In other embodiments, the first end 152 and/or the second end 154 of the engagement member 150 may be affixed to a discrete pull wire, pusher, or other actuator, which may be actuated to effect elongation of the engagement member 150 while the guide catheter 12 and/or the push catheter 14 remain stationary.

The engagement member 150 may be distensible (e.g., stretchable or elongatable) from a first length to a second length, which will be further described herein. The engagement member 150 may be formed of various stretchable materials. In some instances, as shown in FIGS. 4A and 4B, the engagement member 150 may comprise a sleeve circumferentially surrounding the guide catheter 12. The engagement member 150 may be formed of various materials, such as polymeric materials, foam, silicone, rubber, or other stretchable materials. The material of the engagement member 150 may be chosen to provide a desired coefficient of friction between the surface of the engagement member 150 facing the inner surface 49 of the drainage stent 20 and the inner surface 49 of the drainage stent 20. In some embodiments, the engagement member 150 may include surface effects including, but not limited to, grooves, bumps, ridges, holes, dents, ribs, patterns, and the like.

FIG. 4A shows the drainage stent 20 selectively coupled to the guide catheter 12 with the engagement member 150 in a first position. In the first position shown in FIG. 4A, the engagement member 150 is positioned between the inner surface 49 of the drainage stent 20 and the outer surface 13 of the elongate shaft of the guide catheter 12. The surface of the engagement member 150 facing the inner surface 49 of the drainage stent 20 may be frictionally engaged with the inner surface 49 of the drainage stent 20 to prevent disengagement of the drainage stent 20 from the guide catheter 12.

In the first position, the engagement member 150 may have a first length L1 and a first thickness T1. Length, as used herein is a dimension of the engagement member 150 measured in a direction parallel to the central longitudinal axis of the guide catheter 12 and drainage stent 20, and refers to the distance between the first end 152 and the second end 154 of the engagement member 150. Thickness, as used herein is a dimension of the engagement member 150 measured in a radial direction perpendicular to the central longitudinal axis of the guide catheter 12 and the drainage stent 20, and refers to the distance between the surface of the engagement member 150 facing the guide catheter 12 and the surface of the engagement member 150 facing the drainage stent 20.

As shown in FIG. 4A, in the first position, the first thickness T1 of the engagement member 150 may be equal to or greater than the distance between the outer surface 13 of the guide catheter 12 and the inner surface 49 of the drainage stent 20, providing an interference frictional fit therebetween. In embodiments in which the engagement member 150 is an annular sleeve, the sleeve of the engagement member 150 has a first outer diameter at the first length L1 which is greater than or equal to the inner diameter of the drainage stent 20. So configured, the surface of the engagement member 150 facing the inner surface 49 of the drainage stent 20 is a first radial distance from the central longitudinal axis of the drainage stent 20 when at the first length L1. Thus, the surface of the engagement member 150 facing the inner surface 49 of the drainage stent 20 is engaged with the inner surface 49 of the drainage stent 20 to secure the drainage stent 20 on the distal portion of the elongate shaft of the guide catheter 12. The engagement member 150 may be frictionally engaged to the inner surface 49 of the drainage stent 20 in the first position in which the engagement member 150 is at the first length L1, thus providing a first coefficient of friction between the surface of the engagement member 150 facing the inner surface 49 of the drainage stent 20 and the inner surface 49 of the drainage stent 20.

The engagement member 150 may be stretched from the first length L1 to a second length L2 by longitudinal movement generally parallel to the central longitudinal axis of the drainage stent 20 and the guide catheter 12. For instance, the engagement member 150 may be stretched from the first length L1 shown in FIG. 4A to a second length L2 shown in FIG. 4B to release the drainage stent 20 from the engagement member 150 and deploy the drainage stent 20. The second length L2 is greater than the first length L1. The Poisson's ratio of the material of the engagement member 150 may be such that as the engagement member 150 is stretched to the second length L2, the thickness of the engagement member 150 is reduced from the first thickness T1 to the second thickness T2, accordingly. For example, the Poisson's ratio of the material of the engagement member 150 may be about 0.1 to about 0.5, about 0.2 to about 0.5, about 0.25 to about 0.45, about 0.3 to about 0.45, or about 0.3 to about 0.5 in some instances.

When the engagement member 150 is stretched to the second length L2, the engagement member 150 may be sufficiently disengaged from the inner surface 49 of the drainage stent 20 to release the drainage stent 20 from the distal portion of the elongate shaft of the guide catheter 12 such that the guide catheter 12 may be withdrawn from the drainage stent 20.

As shown in FIG. 4B, the second thickness T2 of the engagement member 150 may be less than the first thickness T1 of the engagement member 150. The second thickness T2 may be less than the distance between the outer surface 13 of the guide catheter 12 and the inner surface 49 of the drainage stent 20. Thus, when the engagement member 150 is stretched to the second length L2, the surface of the engagement member 150 facing the inner surface 49 of the drainage stent 20 is a radial distance from the central longitudinal axis of the guide catheter 12 and drainage stent 20 less than the radial distance of the surface when the engagement member 150 is at the first length L1. Thus the radial distance of the surface of the engagement member 150 when at the second length L2 may be less than the radial distance to the inner surface 49 of the drainage stent 20. In instances in which the engagement member 150 is an annular sleeve, the outer diameter of the engagement member 150 within the lumen 48 of the drainage stent 20 at the second length L2 may be less than the inner diameter of the drainage stent 20. Thus, the surface of the engagement member 150 facing the inner surface 49 of the drainage stent 20 is sufficiently disengaged from the inner surface 49 of the drainage stent 20 to release the drainage stent 20 from the distal portion of the elongate shaft of the guide catheter 12. For instance, the coefficient of friction between the surface of the engagement member 150 facing the inner surface 49 of the drainage stent 20 and the inner surface 49 of the drainage stent 20 may be reduced through stretching the engagement member 150 from the first length L1 to the second length L2, providing a second coefficient of friction between the surface of the engagement member 150 facing the inner surface 49 of the drainage stent 20 and the inner surface 49 of the drainage stent 20 at the second length L2. In some instances, the surface of the engagement member 150 facing the inner surface 49 of the drainage stent 20 may be spaced away from the inner surface 49 of the drainage stent 20, and thus not frictionally engaged with the inner surface 49 of the drainage stent 20, when at the second length L2.

In some instances, the engagement member 150 may include an adhesive or tacky surface to enhance the coefficient of friction when at the first length L1. Adhesion of the adhesive coating may be enhanced with surface roughening, plasma treatment, electrostatic charge, etc. Similar to the embodiment described regarding FIGS. 3A-3C, in embodiments in which the engagement member 150 includes an adhesive or tacky outer surface facing the inner surface 49 of the drainage stent 20, adhesion between the inner surface 49 of the drainage stent 20 and the engagement member 150 may be reduced as the engagement member 150 is stretched to the second length L2 from the first length L1. When the engagement member 150 is stretched to the second length L2, the engagement member 150 may be debonded or spaced away from the inner surface 49 of the drainage stent 20 such that the drainage stent 20 may be released from the guide catheter 12.

In order to allow elongation of the engagement member 150 it may be necessary to allow at least a portion of the engagement member 150 to move longitudinally relative to the guide catheter 12 and/or the push catheter 14. For instance, as shown in FIG. 4B, to stretch the engagement member 150 the guide catheter 12 may be actuated distally relative to the drainage stent 20 and the push catheter 14. As the guide catheter 12 is actuated distally, the engagement member 150 is stretched from the first length L1 to the second length L2 as the first end 152 of the engagement member 150 is moved away from the second end 154 of the engagement member 150. To effectuate elongation of the engagement member 150, the second end 154 (proximal end) may be fixedly attached to the push catheter 14 while the first end 152 (distal end) is fixedly attached to the guide catheter 12. Thus, the first end 152 may move distally with the guide catheter 12 while the second end 154 may remain stationary relative to the push catheter 14 and the drainage stent 20. As the engagement member 150 is stretched, the coefficient of friction between the surface of the engagement member 150 facing the inner surface 49 of the drainage stent 20 and the inner surface 49 of the drainage stent 20 is reduced until the drainage stent 20 may be released from the engagement member 150.

It is noted that although the above discussion contemplates the guide catheter 12 being actuated in a distal direction relative to the drainage stent 20 to effect release of the drainage stent 20 from the engagement member 150, in some instances the push catheter 14, attached to the second end 154 of the engagement member 150, may be actuated proximally relative to the drainage stent 20 to effect release of the drainage stent 20 from the engagement member 150. In such instances, the first end 152 (distal end) of the engagement member 150 may be fixedly attached to the guide catheter 12 while the second end 154 (proximal end) is fixedly attached to the push catheter 14 and moveable relative to the guide catheter 12. Furthermore, it is contemplated that the engagement member 150 may alternatively be stretched by actuating another elongate member attached to either the first end 152 or the second end 154 of the engagement member 150. For instance, a discrete pull wire may be attached to the second end 154 of the engagement member 150 which may be pulled proximally to stretch the engagement member 150 from the first length L1 to the second length L2 while the guide catheter 12 and the push catheter 14 remain stationary, or a discrete pusher may be attached to the first end 152 of the engagement member 150 to stretch the engagement member 150 distally while the guide catheter 12 and/or the push catheter 14 remain stationary.

In some embodiments, the engagement member 50, 150 may be initially arranged in a compressed mode between the inner surface 49 of the drainage stent 20 and the guide catheter 12 and upon delivery to the target location compression is released such that the outer diameter of the engagement member 50, 150 is reduced to less than the inner diameter of the drainage stent 20 in order to release the drainage stent 20 from the guide catheter 12, and thus deploy the drainage stent 20.

In some embodiments, a wire, shim, extrusion, member or other device may be initially inserted between the engagement member 50, 150 and the guide catheter 12 to urge the engagement member 50, 150 into contact with the inner surface 49 of the drainage stent 20. This component may then be removed or withdrawn from between the engagement member 50, 150 and the guide catheter 12 to allow the engagement member 50, 150 to move away from the drainage stent 20 to release the drainage stent 20 from the guide catheter 12, and thus deploy the drainage stent 20.

Figure 5A:
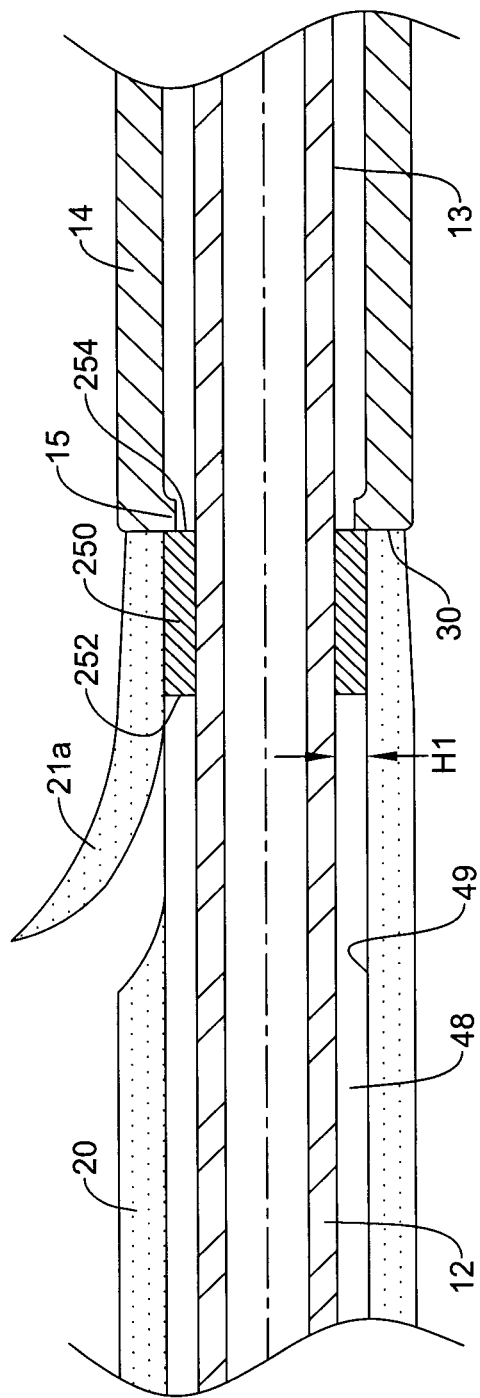
FIGS. 5A and 5B are longitudinal cross-sectional views illustrating the configuration and functionality of another retention structure for selectively coupling a stent to an elongate shaft of a delivery system.
Figure 5B:
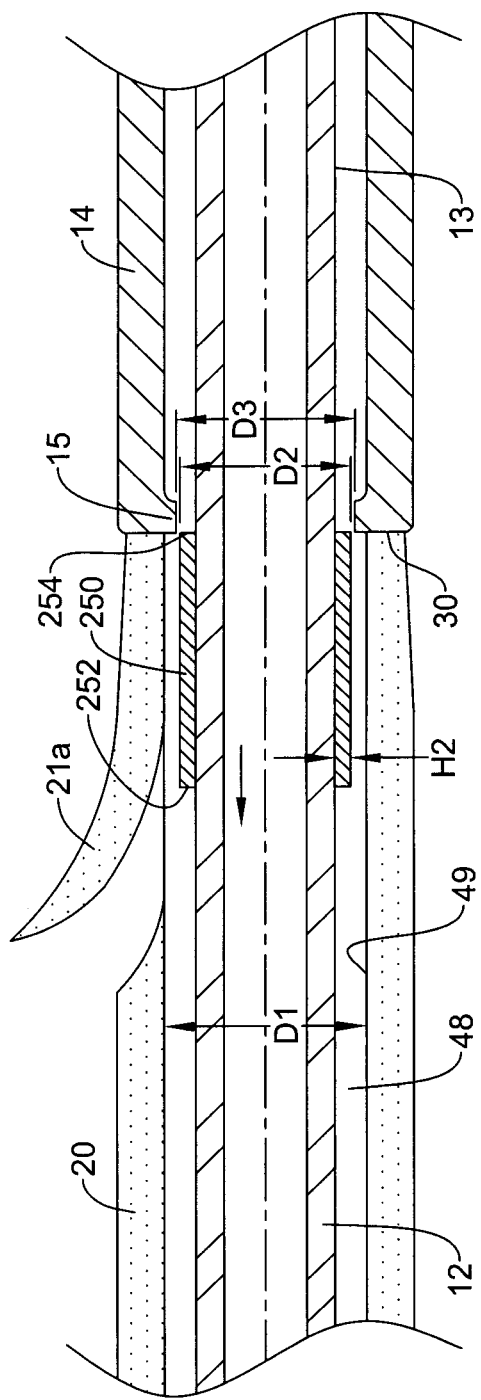

FIGS. 5A and 5B illustrate the components and functionality of a third exemplary retention structure for selectively coupling the drainage stent 20 to an elongate shaft of the drainage stent delivery system 10. Although the drainage stent 20 is illustrated as being selectively coupled to the guide catheter 12 of the drainage stent delivery system 10, it is understood that in some embodiments the drainage stent 20 may be selectively coupled to the push catheter 14, or another elongate shaft, in the manner described with regard to FIGS. 5A and 5B.

As shown in FIG. 5A, a distal portion of the guide catheter 12 extends distally from the distal end 30 of the push catheter 14 into and/or through the lumen 48 of the drainage stent 20. The drainage stent delivery system 10 may include an engagement member 250 positioned on the guide catheter 12 for selectively securing the drainage stent 20 to the guide catheter 12. In some instances, the engagement member 250 may be an annular sleeve circumferentially surrounding the elongate shaft of the guide catheter 12. In other embodiments, the engagement member 250 may be one or more, or a plurality of, interconnected or disconnected elongate members, such as elongated longitudinal strips, positioned on a portion of the guide catheter 12. The engagement member 250 may have a first end 252 and a second end 254 opposite the first end 252 and defining a length therebetween. The engagement member 250 may be positioned on the guide catheter 12 such that one of the first end 252 and the second end 254 is fixedly secured to the guide catheter 12. For instance, as shown in FIGS. 5A and 5B, the first end 252 (i.e., the distal end) of the engagement member 250 may be affixed to the guide catheter 12 while the second end 254 may be movable relative to the guide catheter 12 such that the length of the engagement member 250 may be changed. In other embodiments, the first end 252 and/or the second end 254 of the engagement member 250 may be affixed to a discrete pull wire, pusher, or other actuator, which may be actuated to adjust the length of the engagement member 250 while the guide catheter 12 and/or the push catheter 14 remain stationary.

The engagement member 250 is contractable and/or compressible from a first length to a second length, which will be further described herein. In some instances, as shown in FIGS. 5A and 5B, the engagement member 250 may comprise a sleeve circumferentially surrounding the guide catheter 12. The engagement member 250 may be formed of various materials and/or structures which allow the engagement member to be contracted and/or compressed to urge the engagement member 250 radially outward into engagement with the inner surface 49 of the drainage stent 20. The engagement member 250 may be formed of various materials, such as polymeric materials, foam, silicone, rubber, or other compressible materials, or additional materials such as metallic materials, textiles, etc. which may be deflectable and/or contractable. In some embodiments, the engagement member 250 may include surface effects including, but not limited to, grooves, bumps, ridges, holes, dents, ribs, patterns, and the like.

The engagement member 250 may be configured to be move radially outward from the central longitudinal axis of the guide catheter 12 into engagement with the drainage stent 20 consequent contracting and/or compressing the length of the engagement member 250. In some instances, the engagement member 250 may be a bellows, corrugated member, helical spring, leaf spring, linkage, inflatable member, foam member, polymer member, or other structure whose radial extent may be increased by contracting the ends 252, 254 of the engagement member 250 toward one another.

FIG. 5A shows the drainage stent 20 selectively coupled to the guide catheter 12 with the engagement member 250 in a first position. In the first position shown in FIG. 5A, the engagement member 250 is positioned between the inner surface 49 of the drainage stent 20 and the outer surface 13 of the elongate shaft of the guide catheter 12. The surface of the engagement member 250 facing the inner surface 49 of the drainage stent 20 may be pressed against and frictionally engaged with the inner surface 49 of the drainage stent 20 to prevent disengagement of the drainage stent 20 from the guide catheter 12.

The engagement member 250 may be deflected, compressed, contracted or otherwise moved into the first position shown in FIG. 5A from an equilibrium configuration by applying a force onto the engagement member 250. In order to allow contraction and/or compression of the engagement member 250, it may be necessary to allow at least a portion of the engagement member 250 to move longitudinally relative to the guide catheter 12 and/or the push catheter 14. For example, a force may be exerted onto the engagement member 250 to move the ends 252, 254 of the engagement member 250 closer together to urge the engagement member 250 into the first position.

One possible configuration for exerting a force onto the engagement member 250 to deflect, compress, contract, or otherwise move the engagement member 250 into the first position is shown in FIG. 5A. In such a configuration, the second end 254 of the engagement member 250 may be attached or contact a portion of the push catheter 14. For example, the second end 254 of the engagement member 250 may abut a rim 15 of the push catheter 14 at the distal end 30 of the push catheter 14. As the second end 254 of the engagement member 250 may not be fixed to the guide catheter 12, relative movement between the guide catheter 12 and the push catheter 14 may reduce the distance between the first end 252 and the second end 254 of the engagement member 250 to urge the engagement member 250 to the first position. A locking mechanism, such as the locking mechanism in the handle assembly 16 shown in FIGS. 1 and 2, may be engaged to prevent relative movement between the guide catheter 12 and the push catheter 14 in order to maintain the engagement member 250 in the first position. When desired, the locking mechanism may be unlocked at which point the relative movement between the guide catheter 12 and the push catheter 14 may be permitted. When movement between the guide catheter 12 and the push catheter 14 is permitted, the engagement member 250 may automatically or manually revert to the second position, shown in FIG. 5B, which may be an equilibrium configuration in some instances.

In the first position, the engagement member 250 may have a first length L1 and a first radial height H1. Length, as used herein is a dimension of the engagement member 250 measured in a direction parallel to the central longitudinal axis of the guide catheter 12 and drainage stent 20, and refers to the distance between the first end 252 and the second end 254 of the engagement member 250. Height, as used herein is a dimension of the engagement member 250 measured in a radial direction perpendicular to the central longitudinal axis of the guide catheter 12 and the drainage stent 20, and refers to the distance between the outer surface 13 of the guide catheter 12 and a radially outer extent of the engagement member 250 facing the drainage stent 20.

As shown in FIG. 5A, in the first position, the first height H1 of the engagement member 250 may be equal to or greater than the distance between the outer surface 13 of the guide catheter 12 and the inner surface 49 of the drainage stent 20, pressing the engagement member 250 against the inner surface 49 of the drainage stent 20 and providing an interference frictional fit therebetween. In embodiments in which the engagement member 250 is annular, the engagement member 250 has a first outer diameter at the first length L1 which is greater than or equal to the inner diameter of the drainage stent 20. So configured, the surface of the engagement member 250 facing the inner surface 49 of the drainage stent 20 is a first radial distance from the central longitudinal axis of the drainage stent 20 when at the first length L1. Thus, the surface of the engagement member 250 facing the inner surface 49 of the drainage stent 20 is engaged with the inner surface 49 of the drainage stent 20 to secure the drainage stent 20 on the distal portion of the elongate shaft of the guide catheter 12.

The engagement member 250 may be elongated/and or revert from the first length L1 to a second length L2 by longitudinal movement generally parallel to the central longitudinal axis of the drainage stent 20 and the guide catheter 12. In some instances, the second length L2 may be a length in which the engagement member 250 is in equilibrium in which all compressive forces have been removed from the engagement member 250. Thus, the engagement member 250 may be elongated and/or revert from the first length L1 shown in FIG. 5A to a second length L2 shown in FIG. 5B to release the drainage stent 20 from the engagement member 250 and deploy the drainage stent 20. The second length L2 is greater than the first length L1.

When the engagement member 250 is elongated and/or reverts to the second length L2, the engagement member 250 may be sufficiently disengaged from the inner surface 49 of the drainage stent 20 to release the drainage stent 20 from the distal portion of the elongate shaft of the guide catheter 12 such that the guide catheter 12 may be withdrawn from the drainage stent 20.

As shown in FIG. 5B, the second height H2 of the engagement member 250 may be less than the first height H1 of the engagement member 250. The second height H2 may be less than the distance between the outer surface 13 of the guide catheter 12 and the inner surface 49 of the drainage stent 20. Thus, when the engagement member 250 is elongated and/or reverts to the second length L2, the engagement member 250 is disengaged from the inner surface 49 of the drainage stent 20. Thus the radial extent of the engagement member 250 when at the second length L2 may be less than the radial distance to the inner surface 49 of the drainage stent 20. In instances in which the engagement member 250 is annular, the outer diameter D2 of the engagement member 250 within the lumen 48 of the drainage stent 20 at the second length L2 may be less than the inner diameter D1 of the drainage stent 20. Thus, the engagement member 250 is sufficiently disengaged from the inner surface 49 of the drainage stent 20 to release the drainage stent 20 from the distal portion of the elongate shaft of the guide catheter 12. Furthermore, the second height H2 may be sufficient such that the engagement member 250 may pass into the lumen of the push catheter 14 through the distal opening as the guide catheter 12 is withdrawn proximally. In instances in which the engagement member 250 is annular, the outer diameter D2 of the engagement member 250 at the second length L2 may be less than the diameter D3 of the opening at the distal end 30 of the push catheter 14 such that the engagement member 250, attached to the guide catheter 12, may be withdrawn proximally into the push catheter 14 when the guide catheter 12 is subsequently withdrawn proximally during deployment of the drainage stent 20.

It is noted that although the above discussion contemplates the guide catheter 12 being actuated in a distal direction relative to the drainage stent 20 to effect release of the drainage stent 20 from the engagement member 250, in some instances the push catheter 14 may be actuated proximally relative to the drainage stent 20 to effect release of the drainage stent 20 from the engagement member 250. Furthermore, it is contemplated that the engagement member 250 may alternatively be contracted and/or compressed by actuating another elongate member engaged with either the first end 252 or the second end 254 of the engagement member 250. For instance, a discrete pusher may be engaged with the engagement member 250 to hold the engagement member 250 in the first position. Actuation and/or release of the pusher may allow the engagement member 250 to revert to the second position to allow deployment of the drainage stent 20.

Although several illustrated embodiments of the disclosed stent retention structures are illustrated as being incorporated into a delivery system for delivering a drainage stent, it is understood that the stent retention structures may also be used to selectively couple other stent or endoprosthesis devices to a delivery system. For example, in some instances the stent retention structures described herein may be used to selectively couple a vascular stent to an elongate member of a delivery system for delivering the vascular stent to a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system comprising:
an elongate shaft of a medical device, the elongate shaft having a proximal end and a distal end;
a stent having a proximal end, a distal end, and a central longitudinal axis, the stem positioned on and surrounding a distal portion of the elongate shaft; and
an engagement member having an inner surface and an outer surface, the engagement member positioned between an inner surface of the stent and an outer surface of the elongate shaft, the engagement member configured to be elongated from a first length to a second length greater than the first length by longitudinal movement parallel to the central longitudinal axis of the stent to release the stent;
wherein when at the first length the engagement member has a first thickness measured from a point on the inner surface of the engagement member that is intersected by a line extending radially outward from and perpendicular to the central longitudinal axis to a point on the outer surface of the engagement member that is intersected by the line extending radially outward and perpendicular to the central longitudinal axis, and when at the second length the engagement member has a second thickness measured from a point on the inner surface of the engagement member that is intersected by a line extending radially outward from and perpendicular to the central longitudinal axis to a point on the outer surface of the engagement member that is intersected by the line extending radially outward from and perpendicular to the central longitudinal axis, the second thickness being less than the first thickness;
wherein when at the first length the engagement member is engaged with the inner surface of the stent to secure the stent on the distal portion of the elongate shaft, and at the second length the engagement member is sufficiently disengaged from the inner surface of the stent to release the stent from the distal portion of the elongate shaft such that the elongate shall may be withdrawn from the stent.

2. The stent delivery system of claim 1, wherein the engagement member is a distensible member which is configured to be stretched from the first length to the second length.

3. The stent delivery system of claim 1, wherein the engagement member is a compressible member compressed from an equilibrium configuration when at the first length.

4. The stent delivery system of claim 1, wherein when at the first length a surface of the engagement member is adhesively bonded to the stent.

5. The stent delivery system of claim 4, wherein when at the second length the surface of the engagement, member is debonded from the stent.

6. The stein delivery system of claim 1, wherein when at the first length the engagement member has a first thickness and at the second length the engagement member has a second thickness less than the first thickness.

7. The stent delivery system of claim 6, wherein the first thickness is equal to or greater than a distance between the outer surface of the elongate shaft and the inner surface of the stent, and the second thickness is less than the distance between the outer surface of the elongate shaft and the inner surface of the stent.

8. The stent delivery system of claim 1, wherein the engagement member is a sleeve.

9. The stent delivery system of claim 8, wherein the sleeve includes an adhesive outer surface.

10. The stent delivery system of claim 9, wherein when the sleeve is stretched from the first length to the second length adhesion between the adhesive outer surface and the stent is reduced.

11. The stent delivery system of claim 8, wherein the sleeve is a foam sleeve.

12. The stent delivery system of claim 1, wherein the engagement member is a sleeve having a first outer diameter at the first length and a second outer diameter at the second length, the first outer diameter being greater than or equal to an inner diameter of the stent and the second outer diameter being less than the inner diameter of the stent.

13. A stent delivery system comprising:
a stent including a tubular member having a proximal end, a distal end and a lumen extending therethrough along, a central longitudinal axis of the stent, the lumen defined by an inner surface of the stent;
an elongate shaft extending distally from a handle assembly into the lumen of the stem; and
an engagement member positioned between an outer surface of the elongate shaft and the inner surface of the stent, the engagement member having a first end fixedly attached to the elongate shaft and a second end opposite the first end which is translatable relative to the elongate shaft;
wherein the engagement member is configured to be elongated from a first length to a second length greater than the first length to release the stent from the elongate shaft;
wherein when at the first length the engagement member has a first thickness measured perpendicular to the central longitudinal axis from a point on a surface of the engagement member facing the inner surface of the stent to a point on a surface of the engagement member facing the elongate shaft, and when at the second length the engagement member has a second thickness measured perpendicular to the central longitudinal axis from the point on the surface of the engagement member facing the inner surface of the stent to the point on the surface of the engagement member facing the elongate shaft, the second thickness being less than the first thickness, a line extending radially from and perpendicular to the central longitudinal axis of the stein intersecting the surface of the engagement member facing the elongate shaft at the point on the surface of the engagement member facing the elongate shaft and intersecting the surface of the engagement member facing the inner surface of the stent at the point on the surface of the engagement member facing the inner surface of the stent;
wherein when at the first length the surface of the engagement member facing the inner surface of the stent is a first radial distance from a central longitudinal axis of the stent and when at the second length the surface of the engagement member facing the inner surface of the stent is a second radial distance from the central longitudinal axis of the stent, the second radial distance being less than the first radial distance.

14. The stent delivery system of claim 13, wherein the engagement member is a distensible member which is configured to be stretched from the first length to the second length.

15. The stent delivery system of claim 13, wherein the engagement member is compressed from an equilibrium configuration when at the first length.

16. The stent delivery system of claim 13, wherein the engagement member is a sleeve;
wherein when the sleeve is at the first length the outer surface of the sleeve is adhesively bonded to the inner surface of the stem to prevent disengagement of the stent from the elongate shaft; and
wherein when the sleeve is at the second length the outer surface of the sleeve is debonded from the inner surface of the stent to allow disengagement of the stent from the elongate shaft.

17. The stent delivery system of claim 13, wherein the engagement member is a tubular sleeve;
wherein when the sleeve is at the first length the outer surface of the tubular sleeve frictionally engages the inner surface of the stent providing a first coefficient of friction between the outer surface of the sleeve and the inner surface of the stent to prevent disengagement of the stent from the elongate shaft.

18. The stent delivery system of claim 17, wherein when the sleeve is at the second length, either:
i) a second coefficient of friction less than the first coefficient of friction is provided between the outer surface of the sleeve and the inner surface of the stent which allows disengagement of the stent from the elongate shaft; or
ii) the outer surface of the sleeve is disengaged from the inner surface of the stent.

19. A method of selectively releasing a stent from an elongate shaft of a medical device, the method comprising:
positioning a stent disposed on a distal portion of an elongate shaft of a medical device at a target location of an anatomy, the stent having a central longitudinal axis;
elongating an engagement member positioned between an inner surface of the stent and an outer surface of the elongate shaft in a direction generally parallel with the central longitudinal axis such that the engagement member is elongated from a first length to a second length greater than the first length, the engagement member having an inner surface facing the outer surface of the elongate shaft and an outer surface facing the inner surface of the stent;

wherein when at the first length the engagement member has a first thickness measured from a point on the inner surface of the engagement, member that is intersected by a line extending radially from and perpendicular to the central longitudinal axis to a point on the outer surface of the engagement member that is intersected by the line extending radially from and perpendicular to the central longitudinal axis, and when at the second length the engagement member has a second thickness measured from a point on the inner surface of the engagement member that is intersected by a line extending radially from and perpendicular to the central longitudinal axis to a point on the outer surface of the engagement member that is intersected by the plane extending radially from and perpendicular to the central longitudinal axis, the second thickness being less than the first thickness; and withdrawing the elongate shaft from the lumen of the stent while the engagement member is elongated to the second length, thereby releasing the stent from the elongate shaft.

20. The method of claim 19, wherein elongating the engagement member includes stretching the engagement member from the first length to the second length.

21. The method of claim 20, wherein when the engagement member is stretched from the first length to the second length, either:
   i) adhesion between the engagement member and the inner surface of the stent is reduced; or
   ii) a coefficient of friction between the engagement member and the inner surface of the stent is reduced.

\* \* \* \* \*